United States Patent
Apple et al.

[11] Patent Number: 5,916,143
[45] Date of Patent: Jun. 29, 1999

[54] BRACHYTHERAPY CATHETER SYSTEM

[76] Inventors: Marc G. Apple, 29801 Warwick Ct., Novi, Mich. 48377; Melvin J. Apple, 2553 NW. 52nd St., Boca Raton, Fla. 33496

[21] Appl. No.: 08/748,698

[22] Filed: Nov. 13, 1996

Related U.S. Application Data

[60] Provisional application No. 60/016,498, Apr. 30, 1996.

[51] Int. Cl.⁶ .................................................. A61N 5/00
[52] U.S. Cl. ................................................................ 600/3
[58] Field of Search ............................................. 600/1–8

[56] References Cited

U.S. PATENT DOCUMENTS

| | | | |
|---|---|---|---|
| 5,059,166 | 10/1991 | Fischell et al. | 600/3 |
| 5,213,561 | 5/1993 | Weinstein | 600/7 |
| 5,302,168 | 4/1994 | Hess | 600/3 |
| 5,429,582 | 7/1995 | Williams . | |
| 5,611,767 | 3/1997 | Williams . | |
| 5,616,114 | 4/1997 | Thornton et al. . | |
| 5,662,880 | 9/1997 | Bradshaw et al. | 600/3 |

FOREIGN PATENT DOCUMENTS

| | | |
|---|---|---|
| 0688580 | 12/1995 | European Pat. Off. . |
| 9304735 | 3/1993 | WIPO . |

*Primary Examiner*—John P. Lacyk
*Attorney, Agent, or Firm*—Richard J. Godlewski

[57] ABSTRACT

A system, apparatus, and method for administering radiation internal to a patient involving a catheter, having disposed therewithin a radiation carrier material such as an inert radioactive gas, like xenon, for the treatment of restenosis after angioplasty, and malignancies. When the catheter apparatus is inflated, it may include a plurality of discrete chambers for transporting the radioactive carrier material, and a plurality of discrete chambers enabling substantial blood flow through the artery during treatment with the prescribed radiation.

24 Claims, 6 Drawing Sheets

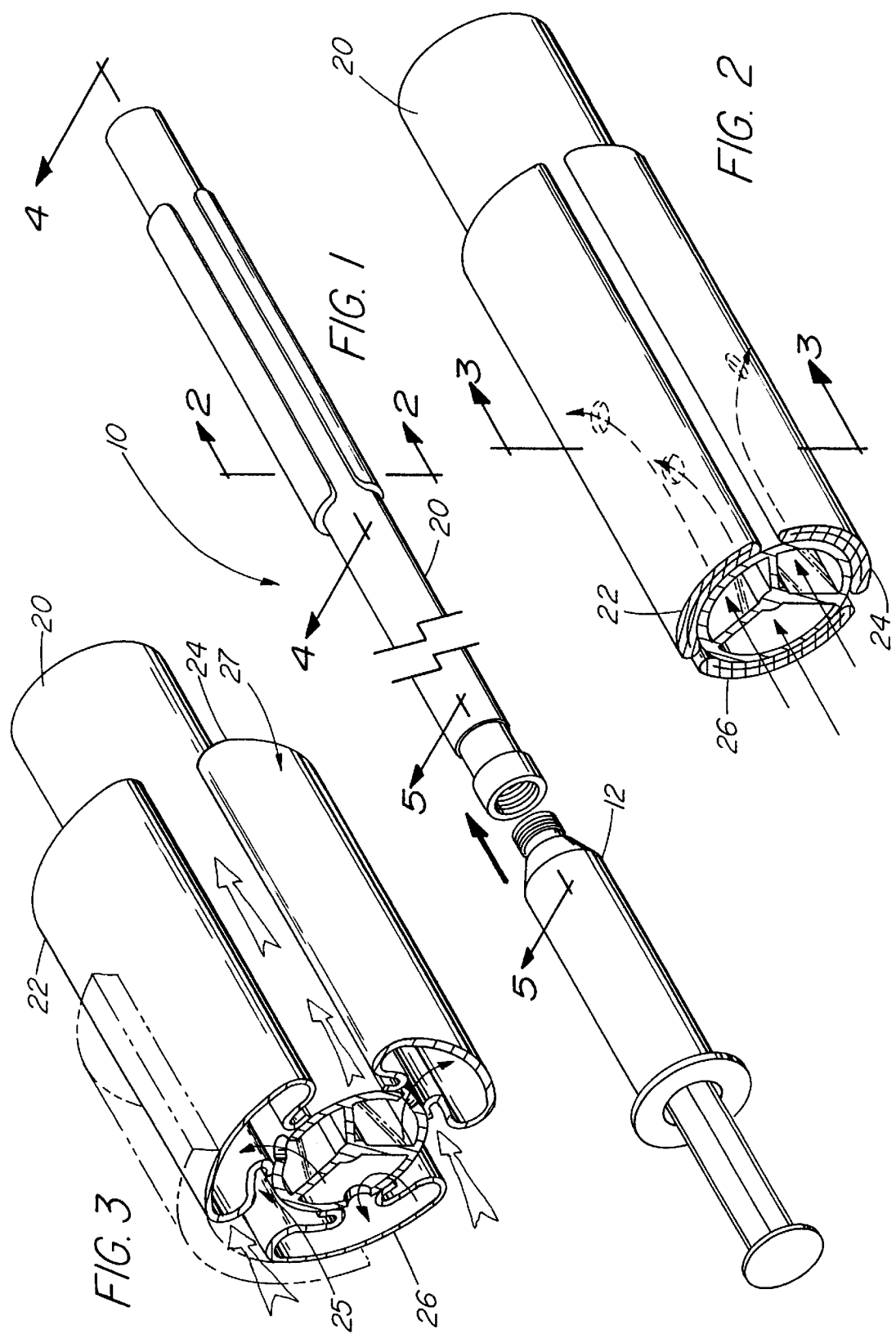

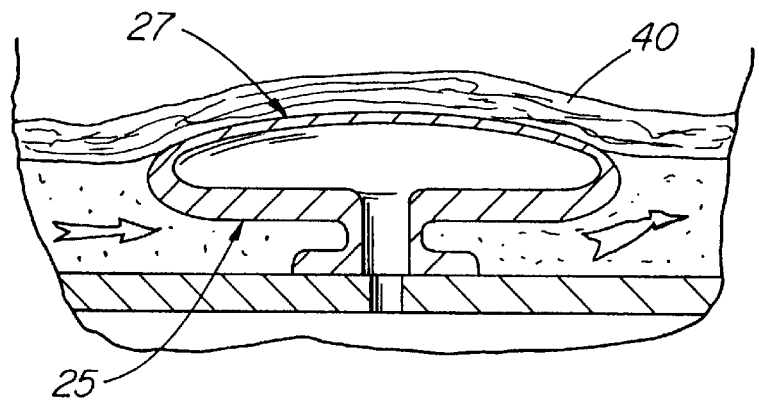
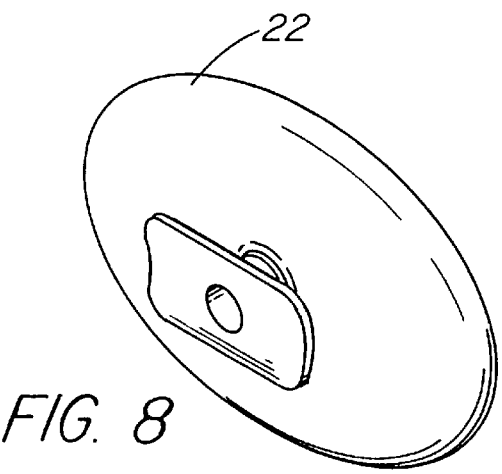
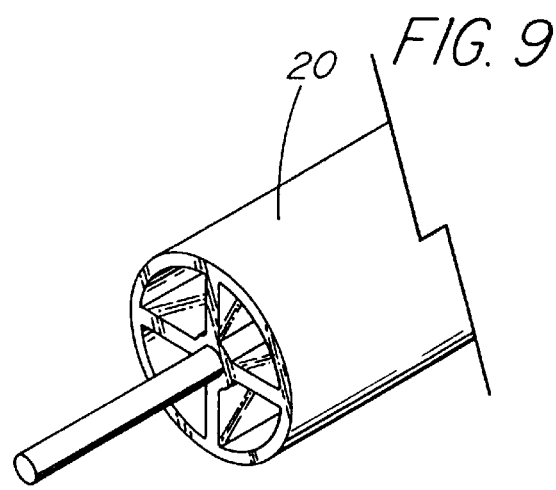
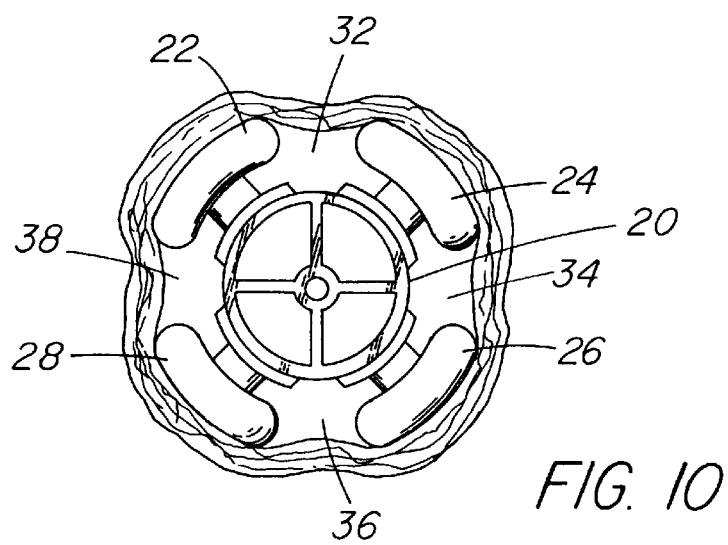

BRACHYTHERAPY CATHETER SYSTEM

This application claims the benefit of U.S. Provisional Application No. 60/016,498 filed on Apr. 30, 1996.

FIELD OF USE

The invention involves a brachytherapy catheter system for administering radiation therapy to a patient by means of a radioactive carrier fluid, more particularly, a radioactive inert gas such as xenon, for treatment of restenosis, malignant or benign tumors, or the like.

BACKGROUND OF THE INVENTION

Angioplasty is an established procedure for removing atherosclerotic plaque from the arterial walls within the vascular system of the patient. The plaque is minimized by use of a catheter that is inserted into the site of the diseased-occluded vessel. A balloon portion of the catheter is then inflated to a predetermined pressure range and size, to radially compress the plaque occlusion, thereby increasing the internal diameter of the previously restricted artery. The balloon is then collapsed and the catheter is removed.

After the angioplasty procedure has been performed, about one-third to one-half of the patients soon develop restenosis. Restenosis is the condition which may occur after angioplasty, with or without stenting, wherein the proliferation of cells cause a restenotic lesion to form, resulting in the further blockage of the intravascular structure.

Various systems and techniques have been devised to treat restenosis:

U.S. Pat. No. 5,059,166 (Fischell et al.) discloses a system for delivering a solid radioactive isotope through a helical coil that is integral with a catheter balloon to inhibit intimal hyperplasia.

U.S. Pat. No. 5,213,561 (Weinstein et al.) discloses a catheter system for preventing restenosis by exposing the lesion to a solid radiation material mounted on the distal end of a guide wire disposed upon a catheter.

U.S. Pat. No. 5,302,168 (Hess) and U.S. Pat. No. 5,411,466 (Hess) disclose a method and an apparatus for restenosis treatment involving a plurality of radioactive elements disposed about the circumference of the catheter, or disposed within the central lumen.

Also, radiation therapy is commonly administered to cancer patients to locally control or destroy malignant tissue. Oftentimes, radiation that is administered to cancer patients externally unavoidably destroys healthy tissue surrounding the tumor.

A system is needed that will:

deliver a predetermined totally-cumulative and homogenous dose of radiation to the lesion site, at a predetermined penetration depth, while minimizing the exposure of surrounding healthy tissue to the radiation;

enable the treating physician or other health-care personnel to be bedside to the patient during the administration of the radiation therapy without exposing the physician or health-care personnel to any reasonable risk;

use radiation material that is readily and inexpensively available from a commercial provider;

use minimal special equipment storage, or delivery devices, except for routine facilities available in most nuclear medicine or radiation oncology departments;

use a radiation carrier material that if applied as an unsealed free-gas form, the inert, noble gas properties essentially enable the molecules of the carrier material to rapidly dissipate throughout the body of the patient without any prolonged organ accumulation or chemical interaction, and rapid dilution of the carrier material is quickly rereleased from the bloodstream through the lungs;

not occlude normal blood flow during therapy, thereby providing more flexibility as to administration time and dosage;

use a radiation carrier material that is a stable and which can be pressurized, stored, and made to high millicurie activity per cubic centimeter with reasonable cost and availability;

use beta particles having excellent initial dose rate delivery and energy transfer when directly adjacent to the targeted tissue with the first one millimeter, and not penetrate much beyond this depth;

use gamma photon energies having decay fractions that provide complementary dose deposition with the beta particles for the first one millimeter, and primary additive dose delivery for an additional two to three millimeters of the targeted tissue; and use beneficial physical and biological radiation properties for treating restenosis, and malignancies (for example—in the brain, lung, esophagus, trachea, cervix, biliary ductal system, colon or rectum, the gastrointestinal system, the gynecological system, or head and neck) and other internal ailments where an internal application of radiation directly applied to the tissue may be needed.

SUMMARY OF THE INVENTION

The system and method of the present invention are useful for the administration of radiation. The intravascular catheter system of the present invention uses either of several unique radiation carrier fluids. The catheter apparatus preferably includes a plurality of balloon sections which are inflated with a radioactive carrier fluid. Residual blood flows through the artery when the balloon sections are inflated through a plurality of sections disposed between the balloon sections. The system can also be readily modified for tissue or organ-specific design to treat malignancies in cancer patients.

The treatment method of the present invention may be applied to a patient either after angioplasty has been performed, or for treating malignant tissue within the brain, lung, esophagus, trachea, cervix, biliary ductal system, colon or rectum, the gastrointestinal system, the gynecological system, or head and neck.

The method is designed to apply ionizing radiation prophylactically to post-angioplasty vascular tissue or tumors internal to a patient while minimizing exposure of healthy tissue. Initially, the location and the size of the tissue to be treated are clinically identified, perhaps, with a fluoroscope. The catheter apparatus is then introduced and positioned adjacent to the tissue to be treated. The catheter apparatus is then inflated with the radioactive fluid exposing the tissue to be treated with radiation. The catheter may include a plurality of discrete balloon sections with special and hypodense material, which enable the inflated catheter to match more closely the internal tissue wall, and minimize the amount of gas loss internal to the patient in the event of leakage. The catheter apparatus includes an outer retractable radiation sleeve or shield to prevent the exposure of healthy tissue to radiation. The radiation shield is then retracted to a specific measurable length. Preferably, the radioactive fluid is an inert gas, such as xenon or an isotope of xenon, and emits beta and gamma particles into the tissue to be treated.

For a more complete understanding of the catheter system, apparatus, and method of the present invention, reference is made to the following detailed description and accompanying drawings in which the presently preferred embodiments of the invention are shown by way of example. As the invention may be embodied in many forms without departing from spirit of essential characteristics thereof, it is expressly understood that the drawings are for purposes of illustration and description only, and are not intended as a definition of the limits of the invention. Throughout the description, like reference numbers refer to the same component throughout the several views.

BRIEF DESCRIPTION OF THE DRAWINGS

FIG. 1 is an assembly drawing of the preferred embodiment of the catheter system of the present invention;

FIG. 2 is a detail sectional view of the deflated catheter apparatus taken along line 2—2 of FIG. 1;

FIG. 3 is a detail sectional view of the fully-inflated catheter apparatus taken along line 3—3 of FIG. 2;

FIG. 7 is a second embodiment disclosing a detail sectional view of a balloon of a catheter apparatus being fully-inflated and having a thickened interior wall and a thinner, hypo-dense outer wall;

FIG. 8 discloses a detail of an inflated balloon of the catheter apparatus as shown in FIG. 7;

FIG. 9 discloses a third embodiment of the catheter apparatus having a removable central lumen guide/ localizing wire that is radio-opaque;

FIG. 10 is a detail sectional view of the fully-inflated catheter apparatus of FIG. 9 within the arterial wall;

DETAILED DESCRIPTION OF THE INVENTION

Figure 4:
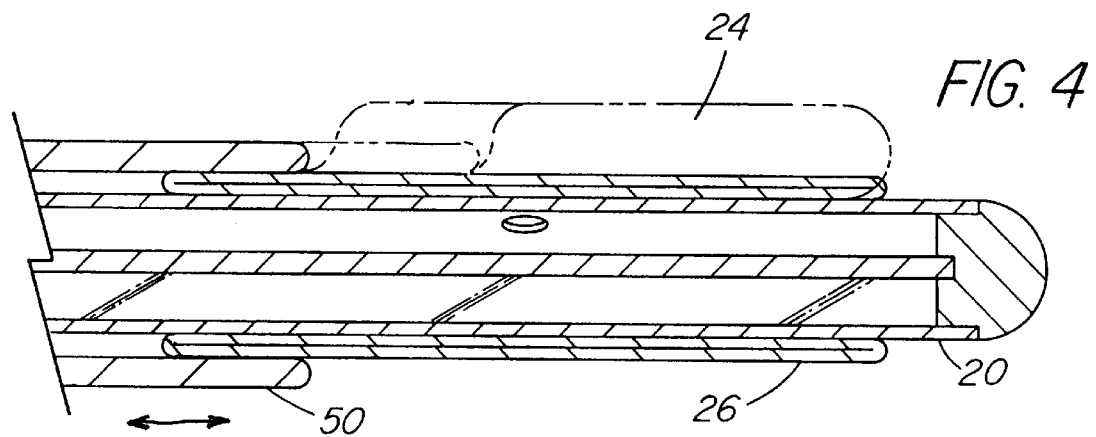
FIG. 4 is a detail sectional view of the deflated catheter apparatus taken along line 4—4 of FIG. 1.
Figure 5:
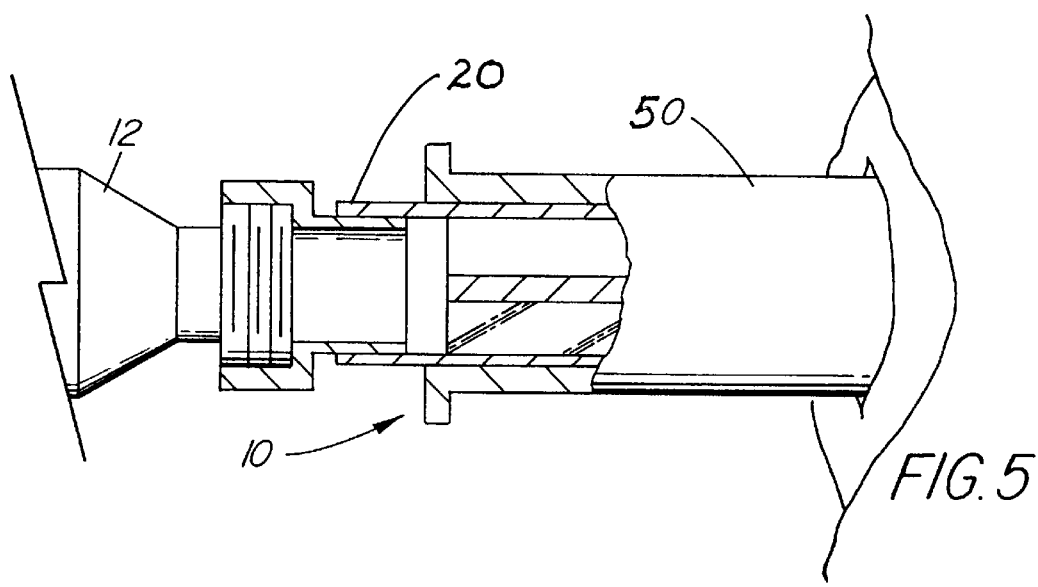
FIG. 5 is an enlarged sectional view of the engagement between the protected, syringed gas supply and the catheter apparatus of FIG. 1.
Figure 6:
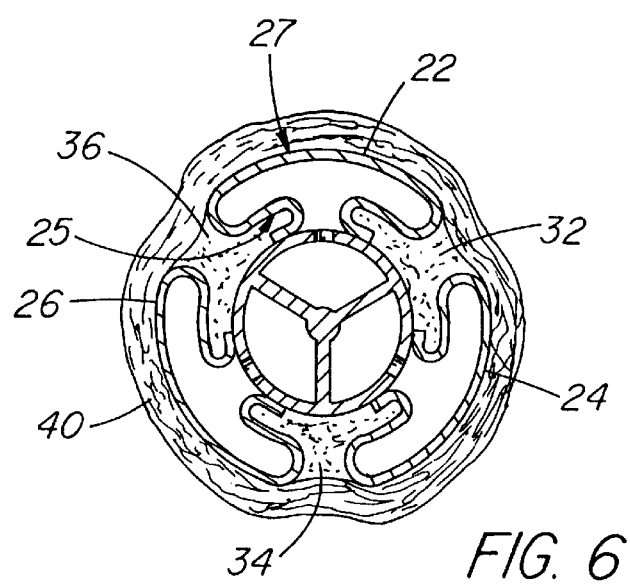
FIG. 6 is a detail sectional view of the fully-inflated catheter apparatus as shown in FIG. 1 inside an arterial wall.
Figure 11:
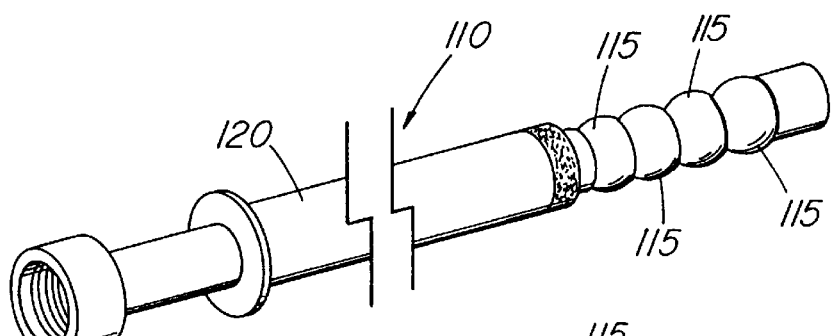
FIG. 11 is an assembly drawing of a fourth embodiment of the catheter system of the present invention with the catheter apparatus being deflated.
Figure 12:
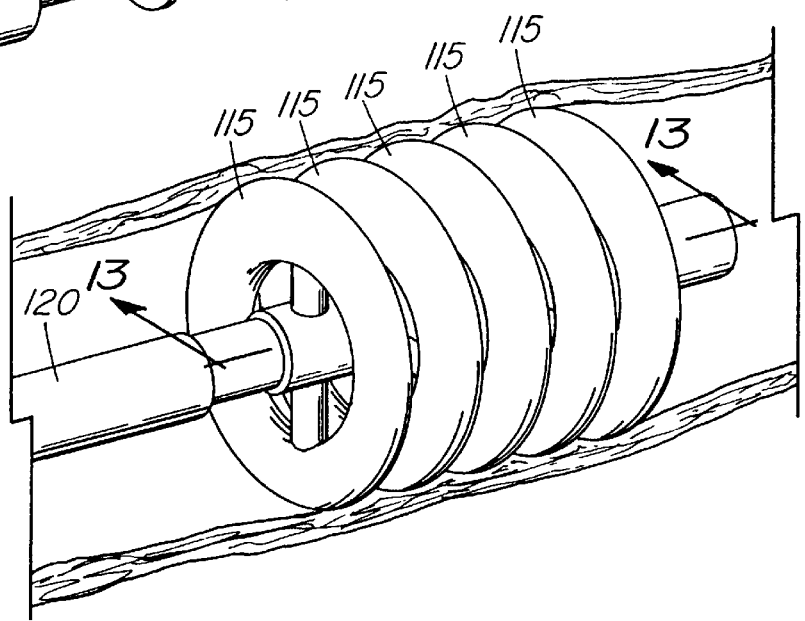
FIG. 12 discloses a detail view of the fully-inflated catheter apparatus of FIG. 11.
Figure 13:
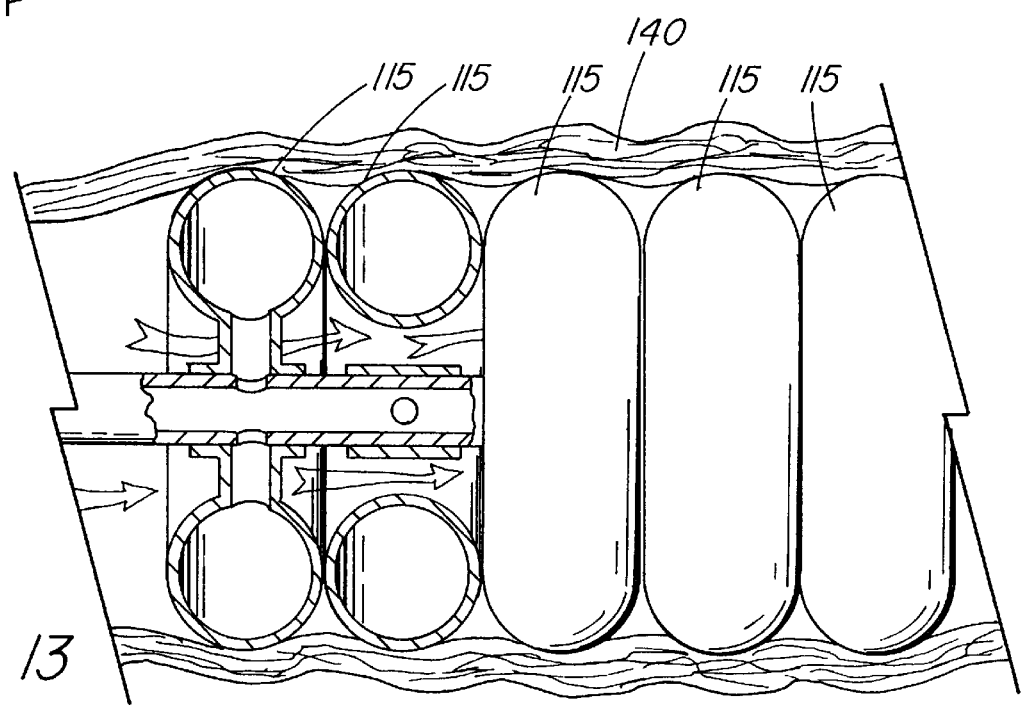
FIG. 13 is a detail sectional view of the fully-inflated catheter apparatus taken along line 12—12 of FIG. 12.
Figure 14:
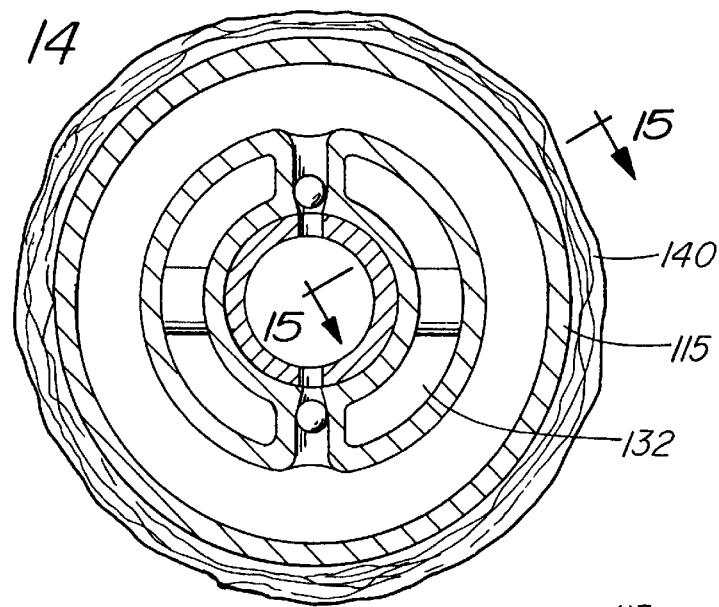
FIG. 14 is a detailed sectional view of the fully-inflated catheter apparatus of FIG. 11.
Figure 15:
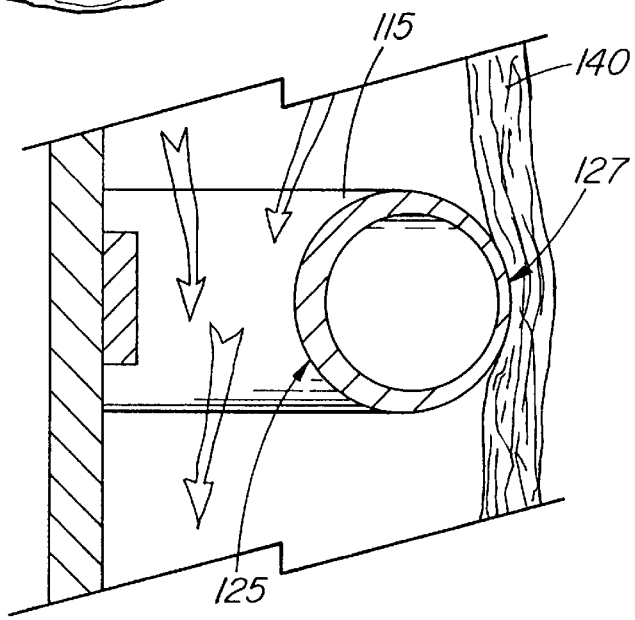
FIG. 15 is an exploded sectional view of a fully-inflated balloon of the catheter apparatus of FIG. 14, the balloon having a thickened inner wall and a thinner hypo-dense outer wall.

FIGS. 1 to 6 disclose the preferred embodiment of the delivery system [10] of the present invention which comprises a supply of radioactive fluid [12] and a catheter apparatus [20]. Preferably, the apparatus [20] is made of latex or similar synthetic compound, commonly used for intravascular applications, and void of any silicon-based or other metal-based materials. The catheter apparatus is disposable after each patient use, and is designed to handle peak expected pressures less than those used in conventional angioplasty (pressures ranging from one to ten atmospheres).

As used herein, the term "fluid" includes any gas, liquid, or gel-type substance that generally conforms to the shape of the container within which it is held, and is fluent. While the catheter apparatus of the present invention is used in conjunction with a radioactive carrier fluid, it is preferred that the fluid is a gas, and for reasons hereinafter set forth, an inert gas, such as xenon, or an isotope of xenon.

The unique intravascular catheter system [10] of the present invention uses a radiation carrier fluid. The catheter apparatus [20] preferably includes a plurality of balloon sections [22, 24, and 26] which are inflated with the radioactive carrier material. Residual blood flows through the artery when the balloon sections [22, 24, and 26] are inflated through a plurality of sections [32, 34, and 36] disposed between the balloon sections.

The method is designed to apply ionizing radiation prophylactically to post-angioplasty vascular tissue or tumors disposed internally within a patient while minimizing exposure of healthy tissue. Initially, the location and the size of the lesion to be treated [40] are clinically identified, perhaps, with a fluoroscope. The catheter apparatus [20] is then introduced and positioned adjacent to the lesion [40]. The plurality of discrete balloon sections [22, 24, and 26] of a special and hypo-dense material enable the inflated catheter apparatus [20] to more closely match the internal tissue wall, and minimize the amount of internal gas loss in the event of leakage. The catheter apparatus [20] includes an outer retractable radiation sleeve or shield [50] to prevent the exposure of healthy tissue adjacent to the lesion to radiation. After the catheter apparatus [20] is positioned alongside the lesion [40], the radiation shield [50] is retracted to a specific measurable length. The balloon sections [22, 24, and 26] are then inflated with the radioactive fluid exposing the lesion [40] to the radiation dosage. The xenon or xenon isotope emit beta and gamma particles into the lesion [40].

The catheter apparatus [20] enables substantial blood or other fluid flow between the balloon sections [22, 24, and 26] when fully inflated. The balloons sections [22, 24, and 26] include a unique inner and outer surface [25 and 27] configuration. The radiation flow is directed through the outer surface [27] of the catheter apparatus [20] to the lesion [40] while exposure to radiation of the blood flowing internal to the catheter apparatus [20] is minimized. Accordingly, the inner surface [25] is more attenuating to the transmission of radiation than the outer surface [27]. Either the inner surface [25] is thicker than the outer surface [27] as shown in FIG. 7, or the inner surface [25] includes a layer of material that is resistant to the penetration of radiation (not shown). Preferably, either three discrete balloon segments are used as shown in FIGS. 1 through 6, or four segments may be used as shown in FIGS. 9 and 10.

One primary application of the system of the present invention is for use after standard, angioplasty procedure:

including multiple lesions at one treatment session. Controlled internal radiation therapy is provided to an artery or vessel for the prevention of arterial restenosis due to smooth muscle hyperplasia or similar related pathology. This will enable cannulation via the same access port from the preemptive dilatation procedure.

Discrete balloon segmented systems [22, 24, and 26] or possible variants are specifically structured to enable the application of a radioactive gas for therapeutic intent.

FIGS. 11 through 16 disclose another embodiment of the catheter apparatus [120] of the present invention. Drafted segmental and peripheral "tire-like" balloon segment configurations [115] optimize direct circumferential abutment of the entire lumen wall. This will minimize intraluminal attenuation factors and maximize homogenous dose rate delivery, conforming and enabling irregularly-shaped intimal surfaces. Also, when the catheter segments [115] are pressurized and expanded, a significant residual rate of intraluminal blood flow is enabled internal to the segments [115].

The catheter apparatus of the present invention is designed to minimize the secondary risk of medical complications caused by blood deficiency due to constriction in the peripheral, kidney, and particularly the heart vessels. The centrally directed perfusion flow may also contribute to outwardly directed pressure gradients, therefore, further supporting and stabilizing the radioactive-gas expander balloons against the arterial wall.

The catheter apparatus of the present invention enables individual patient flexibility as to dosage, treatment exposure time, and lesion segment lengths. Also, since blood flow is not occluded during therapy, radiation time need not be limited to less than three minutes, and therefore, very high energy gamma emitters or activity levels. More expensive loading devices, shielded treatment rooms, and solid radio sources are thereby avoided. Also, healthy tissue is not unnecessarily exposed to passing or placement-preparation time irradiation as with other solid-source systems.

If inadequate blood flow rates or distal symptoms occur, this closed, sealed and inert radioactive gas system [10, 110] may be easily deflated without exposing the patient or medical personnel to real radiation risk.

After flexibly allowing for several minutes of reperfusion time, the catheter apparatus [20, 120] may be simply reinflated and the prescribed treatment time/dose (several times if needed) is resumed without diminishing the therapeutic prophylactic benefit.

Furthermore, the system of the present invention enables the treating therapeutic radiologist to address more than one vessel system or lesion even distal to the distribution of the primary lesion that may require subjective variation in post-dilatation balloon length and diameter due to sensitivity of distal ischemic-prone tissue from risk of prolonged diminished blood flow.

The segmented or compartmentalized radioactive gas delivery tracks communicating with the end point expander balloons, will minimize the potential volume of gas leak should a balloon lose integrity. The residual catheter residing volume may be withdrawn into the shielded syringe without further leakage. The bloodstream released gas poses no real radiation or chemical threat to the patient, because of the physical and biological properties of the inert gas.

Figure 16:
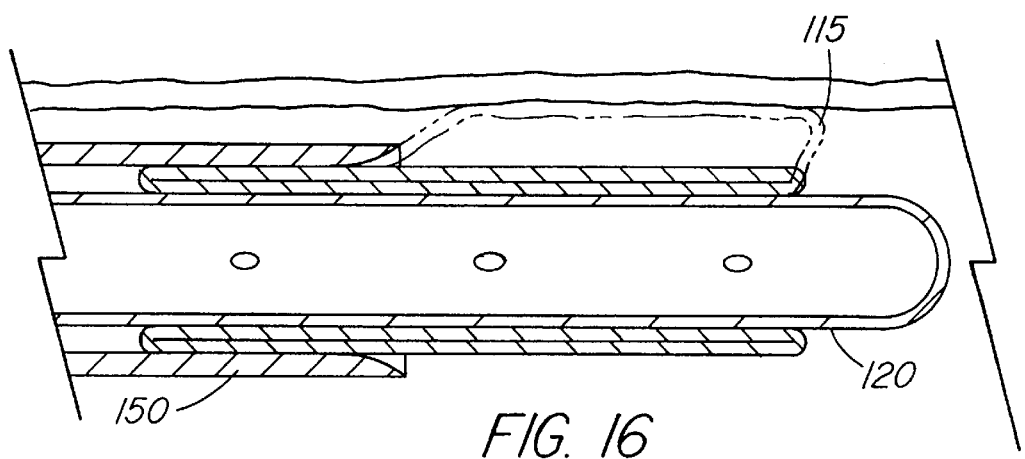
FIG. 16 is a detailed sectional view of the partially-inflated catheter apparatus of FIG. 11, complete with the retractable sleeve.

The length of the distal expandable component of the catheter apparatus [20 or 120] is covered by a thin, retroslidable sleeve [50 or 150], as shown in FIGS. 4 and 16, which is radio-opaque for purposes of imaging localization. The sleeve [50 or 150] is in direct continuity and manipulable externally, to the proximal port of entry controlled and held by the administering physician. After confirmation of placement of the distal catheter apparatus [20 or 120] by fluoroscopic means, the catheter sleeve [50 or 150] is slowly pulled back, and a concordant ruler is exposed in parallel, measured in millimeters, whereby the treating physician accurately determines the length of balloon to be expanded, and the length of the vessel wall to be treated [40 or 140]. This will enable immediate confirmatory calculations as to specific dose rates, treatment time, and the volume of the radioactive gas injected.

The proposed radioactive gas or gases emit gamma photons enabling imaging and semi-log calculations to be performed at bedside using a conventional gamma camera and computer (not shown), which is left on the monitor distal to the treatment field to detect any early leakage for concerned physicians at minimal additional cost.

Although the lumen diameter is narrow and contains only a small fraction of the total volume of radioactive gas injected per session, the designed shielding properties of the sleeve [40 or 140] minimize any significant normal tissue or blood cell exposure over the remaining non-inflated catheter length, particularly with the energies of emission of the isotopes selected.

The interval and possibly staggered placement design of the entry portals and columns between the catheter body and expansion "modules" or balloons enable cutoff control of the balloon expansion length due to the controlled length of outer sleeve retraction.

The primary rationale and benefits for the therapeutic application of radioactive xenon gas with the "ASP" or similar catheters for intravascular brachytherapy enable precise determination of total dose, dose rate, and depth distribution of radiation emitted from a source.

Radioactive xenon-133 gas, and less commonly used xenon-127, have been widely used for several years and proven relatively safe within medically accepted radiation levels for nuclear diagnostic studies involving the lung and the measurement of blood and fluid flow rates through vessels to specific organs. When used as an unsealed free-gas form, the inert, noble gas properties essentially enable the molecules to rapidly dissipate throughout the body of the patient or through a room, without any prolonged organ accumulation or interaction within specific dose ranges. Rapid dilution of the relatively lower energy nuclear emissions of the xenon, is quickly rereleased from the bloodstream through the lungs.

Xenon is a very stable element which can be pressurized, stored, and made to high millicurie activity per cubic centimeter with very reasonable cost and availability. Xenon-133 provides both a beta particle (101 kev avg.; 364 kev max.), and at least two usable photons (32 kev 48 percent; 81 kev 37 percent).

The beta particles offer excellent initial dose rate delivery when directly adjacent to the tissue with the first millimeter. The particle does not penetrate much further beyond the first millimeter of tissue, thereby not contributing to any significant distal normal tissue exposure.

The gamma photon energies and their decay fractions provide complementary dose deposition for the first millimeter, and primary dose delivery for an additional several millimeters of arterial wall and adjacent tissue. The high percent of attenuated, and lower energy photons beyond this point provide for ease of personnel protection with routine lead jackets, or by placing a cover over the external surface of the treated region. Furthermore, the sensitivity of a small field gamma camera provides simple image monitoring and dose evaluation simultaneously.

Xenon-133 is commercially available within a week in concentration ranges from 10 mci to 150 mci per cc or more of gas volume. Also, the cost is currently estimated to be less than a few hundred dollars a dose of 150 mci. A single dose order may be used to treat several patients per day for a full week, as the physical half-life is 5.2 days. Also, no special equipment, storage, or delivery devices are necessary, except for routine facilities available in most nuclear medicine or radiation oncology departments.

In vivo, and in vitro facilities with standard exhaust hoods or positive pressure rooms provide adequate protection for this sealed use of xenon gas. A metered dose can safely and readily be transported to nearly any treatment site by one person, and administered by one person without special radiation protection needs, such as is necessary with higher energy photon sources for conventional brachtherapy. The most expensive addition to a standard treatment room is a simple positive pressure ventilation system, as a backup safety mechanism.

Figure 17:
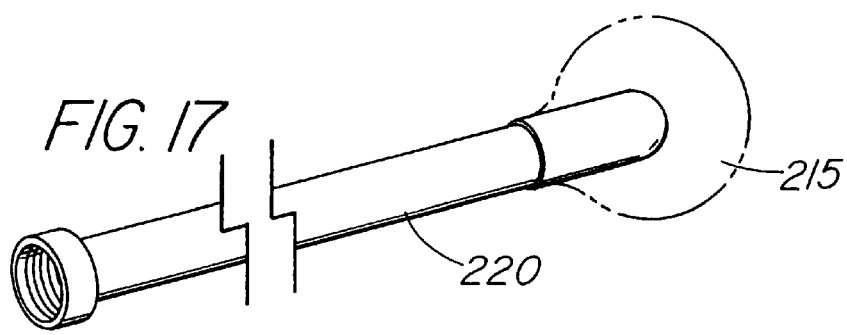
FIG. 17 is a fifth embodiment of the present invention disclosing a deflated catheter apparatus for use in treating malignancies in an organ such as the brain, esophagus, lung, or colon.
Figure 18:
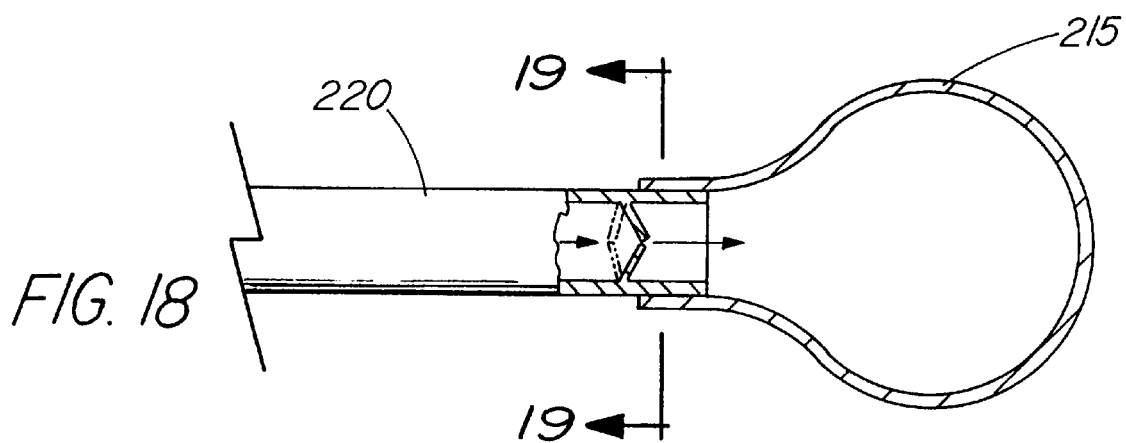
FIG. 18 is a detail view of the inflated catheter apparatus of FIG. 17.
Figure 19:
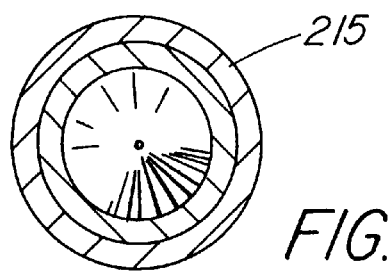
FIG. 19 is a detail sectional view of the pressure-sensitive flapper valve for the inflated catheter apparatus taken along line 19—19 of FIG. 18.

Balloon shaping and customizing design with various thickness and pliable lucent and radiopenetrable material enable site specific, intracavity or intraparenchymal insertion and localization from external origin and placement. FIGS. 17, 18, and 19 illustrate various other applications for the catheter apparatus [220] which may include brain, lung, esophagus, trachea, cervix, biliary ductal system, colon or rectum, the gastrointestinal system, the gynecological system, and head and neck. All would optimize the self introduction of radioactive xenon-133 or others, with controlled expansion and dose rate delivery while enabling individual tissue compliance such that the entire tissue is immediately and homogeneously adjacent to this high or low dose rate source without requiring surgical implant disruption, patient isolation, use of high energy concentrations of other radionuclides, patient or medical personnel risk from leakage, expensive materials, or costly radio-safe suite facilities.

The compliance, stress, and thickness properties of the balloons enable adequate and complete volume expansion against the variable surface of the arterial wall at less pressure than conventional therapeutic dilation plasty catheters, and it is recommended only for use as such.

Furthermore, it is evident that many other alternatives, modifications, and variations of the system, apparatus, and method of the present invention will be apparent to those skilled in the art in light of the disclosure herein. It is intended that the metes and bounds of the present invention be determined by the appended claims rather than by the language of the above specification, and that all such alternatives, modifications, and variations which form a conjointly cooperative equivalent are intended to be included within the spirit and scope of these claims.

We claim:

1. A method for treating tissue inside a patient with radiation while minimizing exposure of healthy tissue, the method comprising the steps of:

providing a catheter apparatus including at least one balloon section structured when inflated to match the shape of the tissue to be treated and to provide homogenous radiation delivery when the balloon section is against the tissue to be treated, the catheter apparatus also including a radiation sleeve to reduce the exposure of healthy tissue to radiation and to control in combination with the balloon section the delivery of radiation to the tissue to be treated;

identifying the location and the size of the tissue to be treated;

introducing the catheter apparatus inside the patient adjacent to the tissue to be treated;

positioning the balloon section of the catheter apparatus adjacent the tissue to be treated;

inflating the balloon section of the catheter apparatus with a radioactive gas other than radon; and removing the radiation sleeve from at least a portion of the balloon section of the catheter apparatus to expose the tissue to be treated with radiation from the radioactive gas other than radon.

2. The method of claim 1, wherein the method further comprises the step of performing an angioplasty procedure on the patient.

3. The method of claim 1, wherein the method further comprises the step of selecting the radioactive gas as inert.

4. The method of claim 1, wherein the method further comprises the step of selecting the radioactive gas as xenon.

5. The method of claim 1, wherein the method further comprises the step of selecting the radioactive gas as an isotope of xenon.

6. The method of claim 1, wherein the radioactive gas other than radon emits beta and gamma particles into the tissue to be treated.

7. The method of claim 1, wherein the method further comprises the step of selecting the tissue to be treated from the group consisting of the brain, lung, esophagus, trachea, cervix, biliary ductal system, colon, rectum, the gastrointestinal system, the gynecological system, head, and neck.

8. A therapeutic delivery system for treating tissue internal to a patient with radiation, the system comprising:

a catheter apparatus for insertion within the body of the patient, the catheter apparatus including a plurality of discrete balloon sections structured when inflated to conform to the tissue to be treated and to provide homogenous radiation delivery when the balloon sections are against the tissue to be treated, the discrete balloon sections being inflatable with a radioactive gas other than radon for providing a homogenous radiation treatment of the tissue to be treated within the body of the patient.

9. The delivery system of claim 8, wherein the delivery system further comprises a radioactive gas other than radon.

10. The delivery system of claim 9, wherein the radioactive gas other than radon emits beta particles into the tissue of the patient.

11. The delivery system of claim 9, wherein the radioactive gas other than radon emits gamma particles into the tissue of the patient.

12. The delivery system of claim 9, wherein the radioactive gas other than radon is inert.

13. The delivery system of claim 9, wherein the radioactive gas other than radon is xenon.

14. The delivery system of claim 9, wherein the radioactive gas other than radon is an isotope of xenon.

15. The delivery system of claim 9, wherein the discrete balloon sections when inflated include an inner surface and an outer surface, the inner surface being more attenuating to radiation than the outer surface.

16. The delivery system of claim 9, wherein the discrete balloon sections when inflated include an inner surface and an outer surface, the outer surface conforming to the tissue of the patient to be treated.

17. A therapeutic delivery system for treating tissue internal to a patient with radiation, the system comprising:

a catheter apparatus for insertion within the body of the patient, the catheter apparatus including at least one balloon section structured when inflated to conform to the tissue to be treated in the patient and to provide homogenous radiation delivery when the balloon section is against the tissue to be treated in the patient, the balloon section being inflatable with a radioactive gas other than radon, beta and gamma particles emitted from the radioactive gas other than radon being useful for treating the tissue in the patient.

18. The therapeutic delivery system of claim 17, wherein the radioactive gas other than radon emits beta particles.

19. The therapeutic delivery system of claim 17, wherein the radioactive gas other radon emits gamma particles.

20. The therapeutic delivery system of claim 17, wherein the therapeutic delivery system further comprises a supply of radioactive gas other than radon.

21. The therapeutic delivery system of claim 17, wherein the balloon sections of the catheter apparatus has an inflated state and a collapsed state, the inflated balloon having an inner surface and an outer surface, the inner surface being more resistant to the transmission of radiation than the outer surface.

22. A catheter apparatus for treating restenosis after angioplasty has been performed on a patient, the apparatus comprising:

a plurality of discrete balloon sections, the balloon sections having an inflated and a deflated state and when in the inflated state structured to conform to the tissue to be treated and to provide homogenous radiation delivery when the balloon sections are against the tissue to be treated, the catheter apparatus including a plurality of sections disposed about the balloon sections for flow of a substantial amount of bodily fluids when the balloon sections are in the inflated state, and the balloon sections of the catheter apparatus when in the inflated state having an inner surface and an outer surface, the inner surface being more resistant to the transmission of radiation than the outer surface.

23. The catheter apparatus of claim 22, wherein the inner surface includes a denser material than a material of the outer surface.

24. The catheter apparatus of claim 22, wherein the inner surface includes a layer of material that attenuates the emission of radiation therethrough.

* * * * *